United States Patent [19]

Terhune et al.

[11] Patent Number: 4,628,252
[45] Date of Patent: Dec. 9, 1986

[54] CORROSIVE IMPURITY SENSOR

[75] Inventors: James H. Terhune, San Jose; Gerald M. Gordon, Soquel, both of Calif.

[73] Assignee: General Electric Company, San Jose, Calif.

[21] Appl. No.: 560,121

[22] Filed: Dec. 12, 1983

[51] Int. Cl.⁴ .......................................... G01R 27/02
[52] U.S. Cl. .................................... 324/65 CR; 73/86; 204/1 T; 204/404; 338/13; 340/603; 422/53; 436/6
[58] Field of Search ............... 340/603, 620, 605; 338/28, 229, 13; 204/1 C, 404; 422/53; 436/6, 149; 324/65 CR, 71.2, 446; 73/86

[56] References Cited

U.S. PATENT DOCUMENTS

| | | | |
|---|---|---|---|
| 2,763,534 | 9/1956 | Campbell | 422/53 |
| 2,803,203 | 8/1957 | Sherwin | 178/70 R |
| 2,864,252 | 12/1958 | Schaschl | 422/53 X |
| 3,116,117 | 12/1963 | Marsh et al. | 422/53 |
| 3,197,724 | 7/1965 | Marsh | 324/65 CR |
| 3,222,920 | 12/1965 | Marsh et al. | 324/65 CR |
| 3,281,833 | 10/1966 | Seidel | 340/691 X |
| 3,846,795 | 11/1974 | Jones | 422/53 X |

Primary Examiner—James L. Rowland
Assistant Examiner—Daniel Myer
Attorney, Agent, or Firm—Ivor J. James, Jr.; Raymond G. Simkins

[57] ABSTRACT

A sensor apparatus cooperates with an electrical system capable of delivering power to and receiving signals from the sensor. A cable housing insulated wires is connected to the sensor and disposed in proximity to a fluid possibly containing a corrosive impurity. Corrosion detecting elements are connected to the wires and are immersed in the fluid possibly containing the impurity. Further, the elements are provided with breakable regions fabricated to corrode in the presence of the corrosive impurity. To facilitate fracture, the elements are loaded in tension so the breakable regions will fracture rapidly in the presence of corrosive impurities, to thereby send an electric signal to remote electrical equipment to indicate the presence of at least one impurity.

1 Claim, 7 Drawing Figures

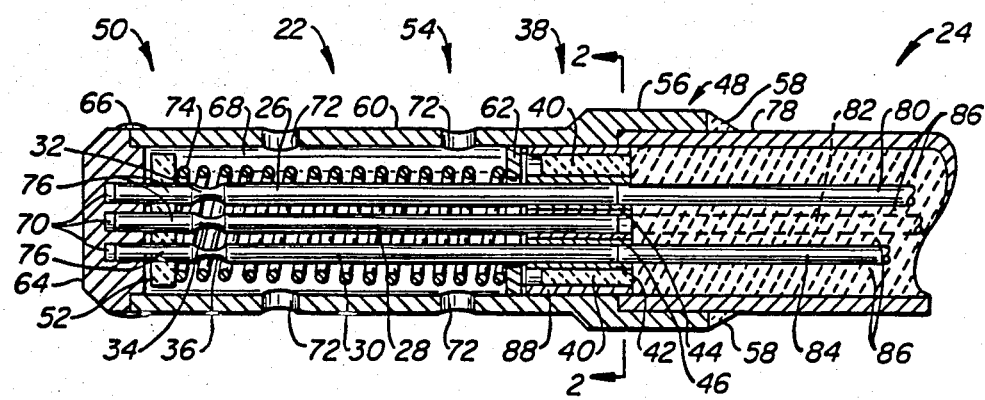
FIG._1.
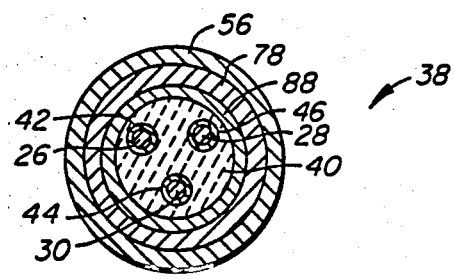
FIG._2.
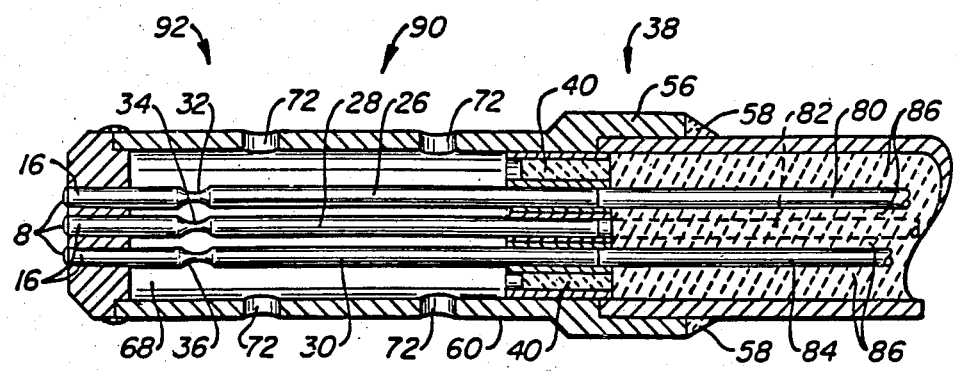
FIG._5.

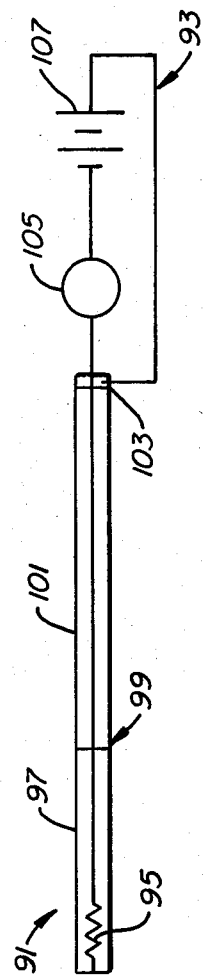
FIG._3.
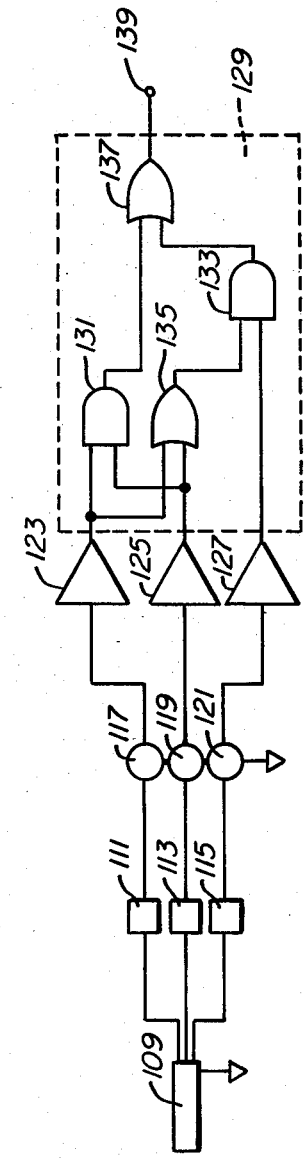
FIG._4.

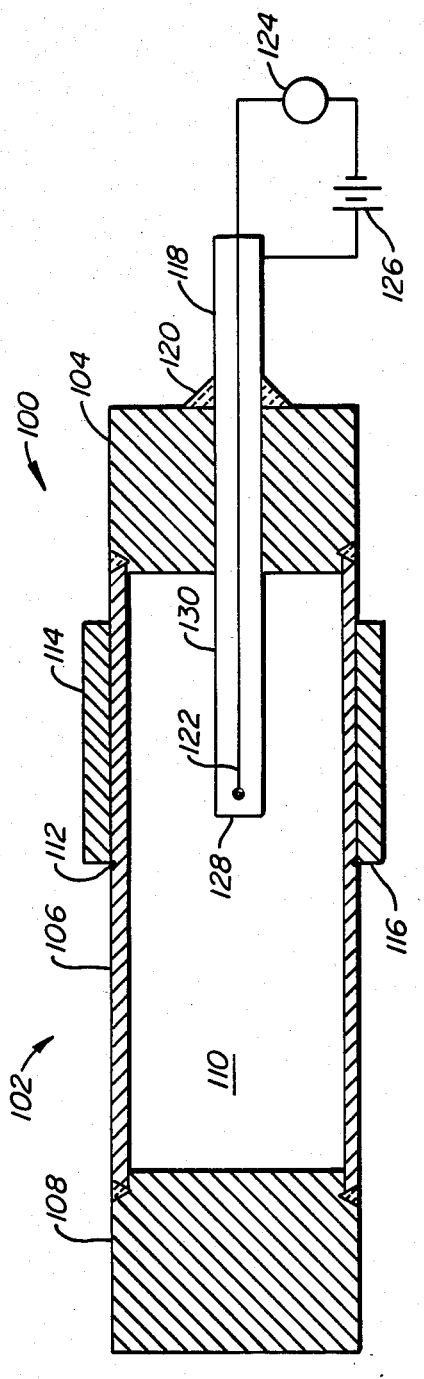
FIG._6.
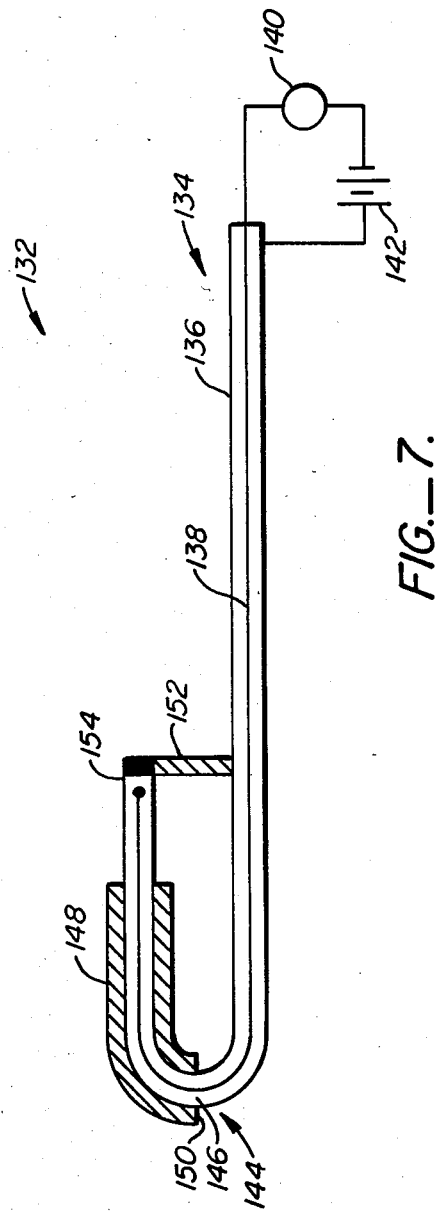
FIG._7.

CORROSIVE IMPURITY SENSOR

BACKGROUND OF THE INVENTION

1. Field of the Invention

This invention relates generally to the detection of impurities in fluids, and more particularly to the detection of corrosive impurities in the core cooling water of nuclear fission light water reactors (LWR).

2. Description of the Prior Art

Stress enhanced intergranular attack has been observed to occur in metal used in LWRs under certain conditions of composition, temperature, stress and configuration. Materials such as 304 stainless steel and Inconel 600 have been observed to be susceptible to cracking and pitting due to this mechanism. Other alloys, especially low carbon stainless steels, are much less susceptible under normal operating circumstances of LWRs. Unfortunately, reactor internals and piping in many LWRs now use materials that suffer from potential intergranular attack.

Materials cracks are also affected measurably by cooling water impurities. LWRs have systems to monitor water purity and maintain the water at acceptable impurity levels under normal operating conditions. However, impurity intrusions occur occasionally, impacting water quality which may or may not have an effect on the LWR system materials. Presently, there are no means for quantitatively measuring the impact of the intrusion events prior to the damaging of the LWR vessel internals, which damage, for example, can occur to the local power range monitors (LPRM) and would become apparent only when the signals emerging from the LPRM's vary erratically or suddenly shift to new relatively constant values.

Sometimes the damage to or failure of LWR vessel internal equipment occurs for reasons other than water impurity. At present it is not possible to determine the cause of such failures in a number of circumstances. This results in reactor shutdown in order to determine if the cause is due to water impurity. The result may be that the reactor shutdown is unnecessary; this is quite costly to the operator of the reactor. Additionally, it would be desirable to know of the presence of impurities in the cooling water well in advance of the impurities causing damage to LWR vessel internals.

Therefore, a need exists for a sensor capable of detecting impurities in LWR cooling water as soon as possible after the impurities are present.

SUMMARY OF THE INVENTION

This invention satisfies the above and other needs by providing an apparatus for measuring impurities in a fluid, with particular interest in LWR cooling water. The sensor apparatus works in combination with an electrical system capable of delivering power to the sensor, and capable of analyzing electric signals produced by the sensor, for detecting the presence of at least one corrosive impurity in the fluid. In a first embodiment, the apparatus comprises an electric signal delivery means, which is electrically insulated from but disposed in proximity to the fluid possibly containing at least one corrosive impurity whose presence is to be determined. A corrosion detecting element means is electrically connected to the electric signal delivery means, and is disposed within the fluid possibly containing at least one corrosive impurity whose presence is to be determined. Further, the corrosion detecting element means is provided with at least one breakable region, selectively fabricated to be breakably corrodable in the presence of at least one corrosive impurity, such that breaking of the element sends an electrical signal to the electrical system which announces the presence of the corrosive impurity. Finally, a tensile loading means is provided for loading the resistive element means in tension, to facilitate corrosive breaking of the resistive element means in the presence of at least one corrosive impurity.

Additional features include apparatus wherein: the corrosion detecting element means are breakably corrodable in the presence of a corrosive impurity selected from the group of halides including chlorides and fluorides; the breakable region comprises at least one necked-down section having a relatively smaller cross-sectional area than the remainder of the element means, and heat treated in the necked-down section to be selectively sensitive to at least one corrosive impurity; the resistive element means is contained in the chamber of a rigid housing, provided with an end cap to enclose the chamber, and further provided with openings through which the fluid with at least one impurity can enter and leave the chamber; the tensile loading means comprises a compressive spring means, connected to place the element means in tension; a second embodiment provides corrosion detecting element means which are secured internally to a housing such that heat expansion of the housing is sufficient to place the element means in tension; at least first, second and third element means are electrically connected to the electric signal delivery means comprising respectively first, second and third wires, such that the electrical system will not react when only one element means breaks, and designed to react when two or more of the element means break.

A third embodiment provides a sensor apparatus, in combination with an electrical system capable of delivering power to the sensor and capable of analyzing the electric signal produced by the sensor, for detecting the presence of at least one corrosive impurity in a fluid. The apparatus comprises a housing in which is disposed a sealed chamber which is pressurized with a gas. The housing is provided with walls having a designed weak area which is relatively weaker than the remainder of the walls. The housing is positioned in a fluid possibly having at least one corrosive impurity, which corrosive impurity if in sufficient concentration will cause the weak area to fracture and admit the corrosive impurity into the chamber.

Further, this third embodiment includes a corrosion detecting element means which penetrates at least one wall of the housing and is electrically insulated from the housing. A portion of the corrosion detecting element means resides within the chamber, and is capable of delivering a signal to the electrical system if the corrosive impurity enters the chamber in sufficient concentration. Variations on this third embodiment provide apparatus wherein: the housing has a cylindrical shape; the gas is an inert gas, for example, helium; and, the weak area is created by enclosing a portion of the housing in an outer tube having an edge adjacent a weak crevice machined around the housing at the contact point of the outer tube edge and the housing.

A fourth embodiment provides a sensor apparatus in combination with an electrical system capable of delivering power to the sensor, and capable of analyzing electric signals produced by the sensor. The sensor apparatus is used for detecting the presence of at least one corrosive impurity in a fluid. The sensor comprises a tube, bent to be stressed below its yield strength, provided with a weak area which is relatively weaker than the remainder of the tube. The tube is positioned in a fluid possibly having at least one impurity which if in sufficient concentration will cause a weak area to fracture. A corrosion detecting element means is disposed within the tube and electrically connected to the electrical system; it is capable of signalling the presence of at least one impurity if the tube fractures.

Additionally, this invention provides a method which, working in combination with an electrical system capable of delivering power to a sensor and capable of analyzing electric signals produced by a sensor, measures the presence of impurities. The inventive method comprises the steps of: (a) fabricating at least one corrosion detecting element to be corrodably breakable by at least one corrosive impurity in a fluid; (b) loading the element in tension; (c) disposing the element in the fluid containing at least one corrosive impurity; and (d) coupling the element to an electrical system capable of signaling the breaking of the element to announce the presence of the corrosive impurity.

BRIEF DESCRIPTION OF THE DRAWINGS

FIG. 1 is a side cutaway view of the sensor in accordance with a first embodiment of the invention;

FIG. 2 is a cross-section taken at line 2—2 of FIG. 1;

FIG. 3 is a schematic diagram of an electric circuit to which each corrosion detecting element is connected;

FIG. 4 is a schematic diagram of a typical voting circuit to which the sensor is connected;

FIG. 5 is a side cutaway view of the sensor according to a second embodiment of the invention;

FIG. 6 is a side cutaway view of the sensor according to a third embodiment of the invention; and FIG. 7 is a side cutaway view of the sensor according to a fourth embodiment of the invention.

DETAILED DESCRIPTION OF THE PREFERRED EMBODIMENTS

Broadly speaking, FIG. 1 provides a sensor system, which includes a subsystem sensor 22 electrically and mechanically coupled to a subsystem cable 24. Internally, sensor 22 is provided with respective first, second and third corrosion detecting elements 26, 28 and 30, each of which is provided with respective first, second and third necked-down regions 32, 34 and 36. In operation, sensor 22 is placed within a fluid such as a gas or LWR cooling water which might contain corrosive impurities. Elements 26, 28 and 30 are placed in tension so that if specified impurities do in fact exist within the cooling water, these impurities will corrode the three elements at the necked-down regions 32, 34 and 36. The tension on the elements 26, 28 and 30 is sufficient to cause the necked-down regions to fracture when corrosion thereof occurs. This sends an electrical signal through cable 24 to an electrical system capable of announcing the presence of the impurities.

More particularly stated, the FIG. 1 and FIG. 2 sensor 22 provide for corrosion detecting element means such as first, second and third elements 26, 28 and 30 which are mounted through an interface to be electrically connected to cable 24. Interface 38 provides a ceramic-to-metal seal comprised of, for example, a ceramic insulator 40; interface 38 also serves as a seal which prevents fluid from flowing out of chamber 68, discussed below. First, second and third respective feed-throughs are mounted within insulator 40, and penetrate through insulator 40 to contact cable end region 48. Elements 26, 28 and 30 are securely mounted within the respective feed-throughs 42, 44 and 46.

Elements 26, 28 and 30 extend outwardly away from interface 38 and are aligned substantially parallel to one another. At some point along the length of the elements, each is provided with respective first, second and third necked-down regions 32, 24 and 36. Using known metallurgical techniques, these necked-down regions are sensitized to be selectively corrodable by pre-selected impurities. The necks are created by precisely machining the elements so that the cross-sectional area of each necked-down region is substantially identical to one another.

It is known in the metallurgical arts that austenitic stainless steels containing carbon in proportions exceeding 0.03% when heated in a certain way become weakened. This is because the carbon, normally in solid solution in the steel, precipitates at the metal crystal grain boundaries. This increased carbon content at the grain boundaries causes the steel to be selectively corrodable by pre-selected corrosive agents. By placing the elements in tension, discussed in detail below, the necked-down regions can be caused to fail rapidly, to thus announce the presence of corrosive impurities. Toward the free end 50 of elements 26, 28 and 30, a thrust tab 52, provided with openings permitting penetration by elements 26, 28 and 30, is slid over and brazed onto the free end 50.

As shown in FIG. 1, sensor 22 is preferably provided with a cylindrical housing 54 to make the sensor 22 more rugged. Housing base 56 fits around the circular cable end region 48 and is securely attached by means such as weld 58. Extending from housing base 56 is housing wall 60. To the inside surface of housing wall 60, in proximity to interface 38, is fastened an annular rigid thrust pad 62. Wall 60 continues to extend away from cable 24, to terminate at its outside end with end cap 64 which is firmly attached to wall 60 by weld 66. The combination of interface 38, wall 60, and cap 64 cooperate to create chamber 68 defined within housing 54. Cap 64 is provided with a plurality of channels 70, designed to accommodate the free outside ends of elements 26, 28 and 30. Wall 60 is provided with a plurality of holes 72, through which fluids are capable of entering and leaving chamber 68.

Surrounding the resistive element means 26, 28 and 30 is a tension loading means in the form of spring 74. Against thrust pad 62 is placed one end of spring 74; the other end of spring 74 rests against thrust tab 52. During assembly, spring 74 is placed in compression against thrust pad 62, and then thrust tab 52 is slid over and around resistive elements 26, 28 and 30 and securely attached to these elements by means of brazes 76. Thus compressed, spring 74 maintains elements 26, 28 and 30 in constant tension. A suitable material from which spring 74 can be fabricated is the alloy Inconel X-750, when properly heat treated according to known metallurgical techniques. This material will have a long service life compared to that of the sensitized elements.

The mechanical design of the necked-down regions 32, 34 and 36 is crucial to the speed of failure of the tension-mounted elements 26, 28 and 30 in the presence of the impurities within the chemical intrusion. Typically the neck stress is just below the yield point under ordinary operating circumstances. As corrosion by the impurity proceeds, the neck is reduced in cross-section area until yielding occurs, followed by fracture. Once one of the elements 26, 28 or 30 fails by tensile fracture, failure of the remaining two elements follows rapidly, because they are subjected to the additional tensile load which was formerly supported by the failed resistive element. Corrosion rates can also be affected by surface conditions and the degree of sensitization of the element material.

The FIG. 1 and FIG. 2 subassembly of cable 24 comprises a steel sheath 78 having a circular cross-section. Disposed within sheath 78 are respective first, second and third wires 80, 82 and 84. Insulation 86 electrically isolates the wires from sheath 78, and may be in the form of a compacted ceramic powder such as silicon dioxide ($SiO_2$) or aluminum oxide ($Al_2O_3$). Wires 80, 82 and 84 terminate at interface 38 by being brazed to the bases of respective elements 26, 28 and 30, to provide an electrical contact between the wires and the elements. Interface 38 is encased in a metallic seal body 88. All the parts comprising interface 38 are tightly fitted together in a manner which prevents any fluid present in chamber 68 from penetrating interface 38 to enter the interior of cable 24.

As shown in FIG. 3 and FIG. 4, the outside end of each wire 80, 82 and 84 is each connected to a separate individual conventional power supply and conventional signal processing electronics, shown and discussed in conjunction with FIG. 3 and FIG. 4. The power supply provides a constant signal through wires 80, 82 and 84 into elements 26, 28 and 30. The signal processing electronics receives a signal from a respective resistive element only if an element breaks, to thereby interrupt the signal delivered by the power system. Elements 26, 28 and 30 are selected to have a low electrical resistance, on the order of a few hundred ohms each under normal operating conditions. However, the resistance is designed to be very high (i.e. open) when the elements 26, 28 and 30 fracture due to stress corrosion cracking. Sensor 22 can be designed to be quite small, typically having an outside diameter of 0.125 inch and an active length of 0.75 inch.

FIG. 3 is a schematic arrangement of one possible electrical connection arrangement for connecting a sensor 91 to an electric circuit 93. Element 95, residing in sensor housing 97, is connected through a seal 99 to a cable 101. Cable 101, through a cable connector 103, is connected to a resistance measurement means 105 such as a conventional ohmmeter, which in turn is connected to a DC power supply 107 whose cathode is connected to cable 101 through connector 103.

FIG. 4 shows a more detailed arrangement wherein three corrosive detecting element means reside within sensor 109, the housing of which is connected to ground. Each of the three individual corrosion detecting resistance elements (not visible in FIG. 4) is connected to its own respective DC power supply 111, 113 and 115, which in turn is connected through individual grounded ohmmeters 117, 119 and 121 to individual signal conditioning analog-to-digital converting amplifiers 123, 125 and 127. These amplifiers are connected to a two-out-of-three voting circuit 129, comprising a conventional electronic connection among two AND gates and two OR gates. These are respectively shown as AND gates 131 and 133, and OR gates 135 and 137. The voting circuit logic will not output a signal at terminal 139 unless at least two of the corrosion detecting element means fracture. Such a fracture would indicate the presence of corrosive materials within the fluid being monitored.

During operation, sensor 22 is disposed within a fluid possibly containing impurities whose presence is to be determined. The fluid including any impurities is permitted to flow into and out of housing chamber 68 through holes 72. Because the necked-down regions 32, 34 and 36 of elements 26, 28 and 30 have been selectively sensitized by heat treatment to respond to particular types of impurities, these necked-down regions will corrode if such impurities exist. Since elements 26, 28 and 30 are loaded in tension by means of spring 74, any corrosion of the necked-down region will cause crack propagation and eventual fracture.

A fracture of one of the elements sends an electrical signal back through the respective wire 80, 82 and 84 to the electric signal analyzer, which announces that at least one element has fractured. The tensile stress is then increased in the other contiguous elements until they also fail due to corrosion. The elements are designed such that any two elements can sustain the tensile stress under normal conditions, but not in the presence of corrosion cracking. Thus, inadvertent failure of a single element will not lead to a false indication of the presence of an impurity. At least two elements must fail before the electronics indicate such failure. This increases the reliability of sensor 22, insofar as other uncorrelated failure modes are concerned, such as failure cause by material defects in the elements.

Reliability is further increased by placing a plurality (not shown) of sensors 22 in the location desired for monitoring the presence of any impurities. If a number of sensors 22 fail close together in time, there is a high probability of the presence of impurities. This information can be used to shut down the operation of the equipment being measured in order to replace or clean the fluid in order to remove any impurities.

The specific application for which this invention has been developed is for measuring the presence of impurities such as the halides including chlorides and fluorides in LWR core cooling water. The three essentially identical elements 26, 28 and 30 are exposed to this coolant water fluid in a flow configuration. The elements are specifically designed to fail rapidly when water purity degrades. The elements are typically composed of Inconel 600, and housing 54 is composed of 316L stainless steel. Inconel 600 is selected because it is susceptible to stress corrosion cracking, and its yield and ultimate strengths are well suited for crack initiation and propagation. On the other hand, the 316L stainless steel alloy is not readily susceptible to intergranular attack.

Sensor 22 is designed to be mechanically stiff so that its resident elements will avoid low cycle fatigue as a result of the vibrations within the core. Therefore, to prevent such low cycle fatigue which would eventually cause failure of the elements, the resonant frequency of the sensor elements is selected to be considerably higher than the vibration frequencies within the core.

FIG. 5 is a second embodiment according to the invention. Cable 24 and interface 38 of FIG. 5 are identical to the like parts in FIG. 1; therefore, it is not necessary to repeat the structure of these parts which were fully described in the FIG. 1 description. Likewise, the FIG. 5 housing wall 60 chamber 68, holes 72, respective elements 26, 28 and 30, and respective necked-down regions 32, 34 and 36 are identical to the like-number parts of FIG. 1.

The main structural difference of FIG. 5 over FIG. 1 is that the FIG. 5 housing 90 provides a sensor 92 which is sealed with an end cap 92 differing from the structure of the FIG. 1 end cap 64. The FIG. 5 end cap 94 is provided with a plurality of penetrations 96 through which the tips of the elements 26, 28 and 30 emerge out the top of end cap 94. Brazes 98 secure the emerging tips of elements 26, 28 and 30 to the end cap.

The key feature of FIG. 5 is that elements 26, 28 and 30 are fabricated from a material having a different coefficient of thermal expansion than that of housing wall 60 and end cap 94. By this arrangement, tension is applied to the elements by in situ heating of the housing wall 60 and the sensor 92, such that housing wall 60 thermally expands laterally away from interface 38 a greater amount than do the elements, to thereby place the elements in tension. For example, 316 L stainless steel can be used as the load frame housing wall 60, and alloy Inconel 600 can be used as the material for fabricating the elements. Sensor 92 is heated in situ by the core cooling water, which is typically at a temperature of approximately 550° F.

FIG. 6 is a third embodiment according to the invention. Sensor 100 comprises a cylindrical housing 102 provided with a base 104, wall 106 and top 108, welded together in sequence to create a sealed chamber 110. A notch 112 is machined around the circumference of the outside of wall 106. Cylindrical tube 114, having an internal diameter equal to the outside diameter of housing 102, is slid over wall 106 and positioned such that edge 116 of tube 114 resides adjacent notch 112. A conduit 118 penetrates base 104 and enters chamber 110, where it is sealed in place by weld 120.

Disposed within conduit 118 is a wire 122, electrically connected to a meter 124 and power supply 126 which is in turn electrically connected to conduit 118. End 128 of conduit 118 opens into chamber 110. Chamber 110 is pressurized with an inert gas such as helium, to thereby place wall 106 of sensor 102 in tension by pressure expansion within chamber 110.

In operation, sensor 100 is placed within the fluid such as the core cooling water suspected of containing impurities. If such impurities are present, these impurities will corrode the notch 112 of sensor 100 so that eventually the wall 106 will fracture at the point where edge 116 and notch 112 meet. The fluid then enters chamber 110 and conduit 118 through end 128, which impurities if present will provide ions capable of conducting a current between side 130 of conduit 118 side 130 and the wire 122. The potential difference existing between side 130 and wire 122 established by power supply 126 produces a current which flows through the ionized fluid, to thereby complete the electric circuit and create a current flow. Meter 124 indicates this current, to thereby indicate the presence of impurities in the cooling water.

FIG. 7 is a fourth embodiment according to the invention. Sensor 132 comprises a sealed cylindrical conduit 134 having a wall 136. Disposed within and electrically isolated from wall 136 is wire 138 which is externally connected to a meter 140 and power supply 142, which in turn is electrically connected to wall 136. By this arrangement, power supply 142 creates a potential difference between wall 136 and wire 138. Conduit 134 is bent to place wall 136 in tension, but is bent such that the yield strength of the material comprising wall 136 is not exceeded. At bent point 144, a notch 146 is machined into a portion of wall 136. A sleeve 148 is formed in tight contact around wall 136 and positioned with edge 150 adjacent notch 146. Anchor 152 is securely fastened to tip 154 of bent conduit 134 and also to wall 136 to firmly secure the bent portion of conduit 134. Such an arrangement places notch 146 in tension.

In operation, sensor 132 is positioned within the fluid expected of having impurities. If the selected impurities are present, they will corrode conduit 134 at notch 146; the tension exerted by the bending of tube 134 causes crack propagation within notch 146. Eventually the impurities will corrode the wall 136 sufficiently to cause the wall to rupture, thereby admitting the fluid with impurities into the interior of conduit 134. The ions of the impurity within the fluid provide an electrical conducting path which will complete the electrical circuit between wall 136 and wire 138. This will produce a current signal which is indicated by meter 140, to thereby indicate the presence of impurities within the fluid.

Numerous advantages are offered by this invention according to the various four embodiments discussed above. The embodiments of FIG. 1, FIG. 2 and FIG. 5 provide a device which is passive, lacks moving parts or gases, compact, rugged and inexpensive to manufacture. These first two embodiments provide a sensor design which includes internal redundancy and two out of three voting logic to discriminate against uncorrelated failure modes of the three elements. The FIG. 5 second embodiment device is self-actuated due to differential thermal stressing of the sensor as it resides in the core reactor water.

All four embodiments of FIGS. 1, 5, 6 and 7 can be designed for rapid response to impurity chemical contaminants in the fluid of the reactor cooling water. All four embodiments can be used in the reactor core or in the coolant piping system (not shown) to give early warning of corrosive impurity conditions. The sensors can readily be replaced following failure due to chemical impurity incursion. The sensors are small and inexpensive enough for use in replication throughout the LWR plant as required.

The foregoing detailed description of the example preferred embodiments of the invention have been presented solely for purposes of illustration and description. This detailed description is not intended to be exhaustive, or to limit the invention to the precise form disclosed. Obviously, many modifications and variations are possible in light of the above teaching. The example preferred embodiments were chosen and described in order to best explain the principles of the invention and its practical applications, to thereby enable others skilled in the art to best utilize the invention in various other embodiments not described above, and with various modifications as are suited to the particular use contemplated. It is intended that the scope of the invention be defined solely by the appended claims.

What is claimed is:

1. A sensor, in combination with an electrical source capable of delivering power to the sensor and meter means capable of indicating an electrical conduction produced by the sensor, for detecting the presence of at least one corrosive impurity in a fluid, the sensor comprising:

(a) a tube, bent to be stressed below its yield strength, provided with a weak groove area at the bend which is relatively weaker than the remainder of the tube, which tube is positioned in a fluid possibly having at least one impurity which if in sufficient concentration will cause the weak area to fracture; and (b) a corrosion detecting element means, disposed within the tube, electrically connected to said electrical source, capable of conducting in the presence of at least one impurity if the tube fractures.

* * * * *